US008507551B2

(12) United States Patent
Nizet et al.

(10) Patent No.: US 8,507,551 B2
(45) Date of Patent: Aug. 13, 2013

(54) ANTIMICROBIAL THERAPY FOR BACTERIAL INFECTIONS

(75) Inventors: Victor Nizet, San Diego, CA (US); George Y. Liu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 11 days.

(21) Appl. No.: 11/918,584

(22) PCT Filed: Apr. 17, 2006

(86) PCT No.: PCT/US2006/014486
§ 371 (c)(1),
(2), (4) Date: Oct. 15, 2007

(87) PCT Pub. No.: WO2007/075186
PCT Pub. Date: Jul. 5, 2007

(65) Prior Publication Data
US 2009/0042976 A1 Feb. 12, 2009

Related U.S. Application Data

(60) Provisional application No. 60/672,359, filed on Apr. 18, 2005.

(51) Int. Cl.
*A61K 31/357* (2006.01)
*A61K 31/216* (2006.01)
*A61K 31/135* (2006.01)
*C12Q 1/02* (2006.01)

(52) U.S. Cl.
USPC .............. 514/464; 514/534; 514/646; 435/29

(58) Field of Classification Search
USPC ............................. 514/464, 534, 646; 435/29
See application file for complete search history.

(56) References Cited

U.S. PATENT DOCUMENTS

| | | | |
|---|---|---|---|
| 3,369,974 A | 2/1968 | Ninet et al. | |
| 3,857,934 A | 12/1974 | Bernstein et al. | |
| 5,877,186 A | 3/1999 | Leef et al. | |
| 5,935,808 A | 8/1999 | Hirschberg et al. | |
| 5,965,553 A | 10/1999 | Bell et al. | |
| 2009/0306021 A1 | 12/2009 | Nizet et al. | |

FOREIGN PATENT DOCUMENTS

| | | |
|---|---|---|
| EP | 0710665 A1 | 5/1996 |
| WO | 2005011567 A2 | 2/2005 |
| WO | 2007075186 A2 | 7/2007 |
| WO | 2007133712 A3 | 11/2007 |

OTHER PUBLICATIONS

Hammond (Inhibition of Carotenoid Hydroxylation in *Staphylococcus aureus* by Mixed-Function Oxidase Inhibitors, Journal of Bacteriology, Sep. 1970, p. 607-610).*
Giffo-Schmitt, Beate, PCT International Preliminary Report on Patentability, Date of Issuance of Report: Oct. 30, 2007, International Application No. PCT/US06/14486, 4 pages.

Baumgartner, Heike, Extended European Search Report, Date of Completion of Search: Jan. 27, 2009, International Application No. PCT/US06/14486, 14 pages.
Hammond, Ray K. et al., "Inhibition of Carotenoid Hydroxylation in *Staphylococcus aureus* by Mixed-Function Oxidase Inhibitors," Journal of Bacteriology, Sep. 1970, pp. 607-610.
Singh, R. P., Piperonyl butoxide as a Protectant Against Potato Spindle Tuber Viroid Infection, Phytopathology, vol. 67, 1977, pp. 933-935.
Springer, Dane M., "Anti-MRSA Cephems. Part I: C-3 Substituted Thiopyridinium Derivatives," Bioorganic & Medicinal Chemistry Letters, Pergamon, Elsevier Science, 2001, pp. 797-801.
Tan, Hiok-Hee et al., "Parasitic Skin Infections in the Elderly: Recognition and Drug Treatment," Drugs & Aging, 2001, pp. 165-176.
Fairlamb et al., "Synthesis and antimicrobial evaluation of farnesyl diphosphate mimetics," Bioorganic Chemistry, 2003, vol. 31, No. 1, pp. 80-97.
Kalinoski et al., "Mechanism of inhibition of yeast squalene synthase by substrate ananlog inhibitors," Archives of Biochemistry and Biophysics, 1999, vol. 368, No. 2, pp. 338-346.
Leon et al., "Isoprenoid biosynthesis as a drug target: biosphosphnate inhibition of *Escherichia coli* K12 growth and synergistic effects of fosmidomycin," J. of Med. Chem., 2006, vol. 49, No. 25, pp. 7331-7341.
Liu et al., "*Staphylococcus aureus* golden pigment impairs neutrophil killing and promotes virulence through its antioxidant activity," J. of Exp. Medicine, Jul. 2, 2005, vol. 202, No. 2, pp. 209-215.
Liu Chia et al., "A cholesterol biosynthesis inhibitor blocks *Staphylococus aureus* virulence," Science, 2008, vol. 319, No. 5868, pp. 1391-1394.
Magnin et al., "Alpha-Phosphonusulfonic acids: Potent and Selective Inhibitors of Squalene Synthase," J. of Med. Chem., 1996, vol. 39, No. 3, pp. 657-660.
Garabatos-Perera J., Extended European Search Report, European Patent Office, May 27, 2010.
Song et al., "Phosphonosulfonates are potent, selective inhibitors of dehydrosqualene synthase and Staphyloxanthin biosynthesis in *Staphylococcus aureus*," J. of Med. Chem. 2009, vol. 52, No. 4, pp. 976-988.
Chong, Yong S. International Search Report and Written Opinion. Application No. PCT/US2007/11466. Mail Date: Oct. 2, 2008.
Lowery, Johanna. Australian Examiner's First Report. Australian Application No. 2006330064. Mail date: Dec. 8, 2010.
Liu, G. Y. et al. "Sword and shield: Linked group B streptococcal β-hemolysin/cytolysin and carotenoid pigment function to subvert phagocyte defense," Proc. Natl. Acad. Sci. USA 101:14491-14496 (2004).

(Continued)

*Primary Examiner* — San-Ming Hui
*Assistant Examiner* — Kathrien Cruz
(74) *Attorney, Agent, or Firm* — Gregory P. Einhorn; Gavrilovich, Dodd & Lindsey LLP

(57) ABSTRACT

The disclosure provides a molecular genetic approach of targeted mutagenesis and heterologous expression, coupled with in vitro and in vivo models of bacterial pathogenesis, to demonstrate that the *S. aureus* pigment is a virulence factor and potential novel target for antimicrobial therapy.

14 Claims, 7 Drawing Sheets

(56) References Cited

OTHER PUBLICATIONS

Nizet, Victor M.D., Curriculum vitae, at http://nizetlab.ucsd.edu/people/NizetCV.pdf.

Tapnikar, Sanjay. Examination Report and Notice of Acceptance of Complete Specification. NZ Patent Application No. 572797. Date of Acceptance May 17, 2011.

Walsh, Penny. Examination Report. NZ Patent Application No. 572797. Date of Mailing Jun. 10, 2010.

Baharlou, Simin, International Preliminary Report on Patentability, Date of Issuance of Report: Nov. 27, 2008, International Application No. PCT/US07/11466.

* cited by examiner

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer crtMupF

<400> SEQUENCE: 1
ttaggaagtg catatacttc ac                                    22

<210> SEQ ID NO 2
<211> LENGTH: 53
<212> TYPE: DNA
<213> ORGANISM: Artificial Sequence
<220> FEATURE:
<223> OTHER INFORMATION: Primer crtMstartR

<400> SEQUENCE: 2

```
ggtggtatat ccagtgattt ttttctccat actagtcctc ctatattgaa atg        53

<210> SEQ ID NO 3
<211> LENGTH: 51
<212> TYPE: DNA
<213> ORGANISM: Artificial Sequence
<220> FEATURE:
<223> OTHER INFORMATION: primer crtMendF

<400> SEQUENCE: 3
tactgcgatg agtggcaggg cggggcgtaa caaagtattt agtattgaag c          51

<210> SEQ ID NO 4
<211> LENGTH: 22
<212> TYPE: DNA
<213> ORGANISM: Artificial sequence
<220> FEATURE:
<223> OTHER INFORMATION: primer crtMdownR

<400> SEQUENCE: 4
ggcaccgtta tacgatcatc gt                                          22

<210> SEQ ID NO 5
<211> LENGTH: 30
<212> TYPE: DNA
<213> ORGANISM: Artificial sequence
<220> FEATURE:
<223> OTHER INFORMATION: primer CrtF

<400> SEQUENCE: 5
cagtctagaa atggcatttc aatataggag                                  30

<210> SEQ ID NO 6
<211> LENGTH: 30
<212> TYPE: DNA
<213> ORGANISM: Artificial sequence
<220> FEATURE:
<223> OTHER INFORMATION: primer CrtR

<400> SEQUENCE: 6
atcgagatct ctcacatctt tctcttagac                                  30
```

ANTIMICROBIAL THERAPY FOR BACTERIAL INFECTIONS

CROSS-REFERENCE TO RELATED APPLICATIONS

This application is a National Stage Application filed under 35 U.S.C. §371, which is based upon and claims priority to International Application No. PCT/US2006/014486, filed Apr. 17, 2006, which application claims priority under 35 U.S.C. §119 to U.S. Provisional Application Ser. No. 60/672,359, filed Apr. 18, 2005, the disclosures of which are incorporated herein by reference.

STATEMENT REGARDING FEDERALLY SPONSORED RESEARCH

This invention was made with government support under Grant No. AI048694 awarded by the National Institutes of Health. The government has certain rights in this invention.

BACKGROUND

Ogston (1881) coined the genus *Staphylococcus* to describe grapelike clusters of bacteria (staphylo=grape, Gr.) recovered in pus from surgical abscesses. Shortly thereafter, Rosenbach (1884) isolated this pathogen in pure culture, and proposed the species name *S. aureus* (golden, Lat.) for its characteristic surface pigmentation in comparison to less virulent staphylococci that normally colonize the skin surface.

Entering its seventh decade, the era of antimicrobial therapy has greatly reduced morbidity and mortality from infectious diseases. However, the emergence of resistant microorganisms has now reached epidemic proportions and poses great challenges to the medical community. Worrisome trends are particularly evident in the pre-eminent Gram-positive bacterial pathogen *S. aureus*, which has become increasingly unresponsive to first-line antibiotic therapies. *S. aureus* is probably the most common cause of life-threatening acute bacterial infections in the world, and is capable of causing a diverse array of diseases, ranging in severity from a simple boil or impetigo to fulminant sepsis or toxic shock syndrome. *S. aureus* is the single leading cause of bacteremia, hospital-related (nosocomial) infections, skin and soft tissue infections, wound infections, and bone and joint infections. It is one of the most common agents of endocarditis and food poisoning.

National prospective surveillance of over 24,000 invasive bacterial isolates show disease-associated *S. aureus* strains with methicillin resistance (MRSA) have increased from 22% in 1995 to 57% currently. MRSA are now frequently identified in community-acquired infections as well as in hospital settings. An urgent need exists for discovery of novel classes of antibiotics to address this genuine public health crisis. A half-century of synthesizing analogs based on <10 antibacterial scaffolds has resulted in the development and marketing of >100 antibacterial agents but, with the exception of the oxazolidinone core, no new scaffolds have emerged in the past 30 years to address the emerging resistance problems.

Developing new classes of antibiotics that target bacterial virulence factors such as the *S. aureus* carotenoid pigment is an approach that has not been utilized to anywhere near its potential. Classic antibiotic approaches attempt to kill or suppress growth of bacteria by targeting essential cell functions such as cell wall biosynthesis, protein synthesis, DNA replication, RNA polymerase, or metabolic pathways. These conventional therapies run a higher risk of toxicity since many of these cell functions are also essential to mammalian cells and require fine molecular distinction between the microbial target and host cell counterpart(s). Second, the repetitive use of the same essential targets means that when a bacterium evolves resistance to a particular antibiotic agent during therapy, it can become simultaneously cross resistant to other agents acting on the same target, even though the bacterium has never been exposed to the other agents. Third, conventional therapies exert a "life-or-death" challenge upon the bacterium, and thus a strong selective pressure to evolve resistance to the antimicrobial agent. Finally, many current antibiotics have very broad spectrums of activity, with the side effect of eradicating many components of the normal flora, leading to undesired complications such as Clostridium difficile colitis or secondary fungal infections (e.g. *Candida*).

The emergence of MRSA has compromised the clinical utility of methicillin and related antibiotics (oxacillin, dicloxacillin) and all cephalosporings (e.g. cefazolin, cephalexin) in empiric therapy of *S. aureus* infections. MRSA often have significant levels of resistance to macrolides (e.g. erythromycin), beta-lactamase inhibitor combinations (e.g. Unasyn, Augmentin) and fluoroquinolones (e.g. ciprofloxacin), and are occasionally resistant to clindamycin, trimethoprim/sulfamethoxisol (Bactrim), and rifampin. In serious *S. aureus* infection, intravenous Vancomycin is the last resort, but there have now also been alarming reports of *S. aureus* resistance to vancomycin, an intravenous antibiotic commonly used to treat MRSA.

New anti-MRSA agents such as linezolid (Zyvox or quinupristin/dalfopristin (Synercid), both of which utilize the traditional target of binding to the ribosomal subunits to inhibit RNA synthesis, are quite expensive.

Subsequent studies of the *S. aureus* pigment have unraveled an elaborate biosynthetic pathway that produces a series of carotenoids. Similar carotenoids produced in dietary fruits and vegetables are well recognized as potent antioxidants by virtue of their free radical scavenging properties and exceptional ability to quench singlet oxygen.

SUMMARY

The invention demonstrates that carotenoids serve as virulence/resistance factors in microbes. In one specific example, the invention demonstrates that *S. aureus* carotenoid is a virulence factor that impairs neutrophil killing and promotes disease pathogenesis by virtue of its antioxidant properties, and (2) evidence that pharmacological inhibition of the carotenoid pigment production renders the organism more susceptible to oxidants and blood killing.

The invention provides a method of treating a bacterial infection, comprising administering to a subject inflicted with the infection an agent that inhibits the production and/or activity of a carotenoid in the bacteria. In one embodiment, the bacterial infection is a *Staphylococcus* infection. In another embodiment, the bacteria is a *Staphylococcus* sp. In yet a further embodiment, the bacteria is *Staphylococcus aureus*.

The invention also provides a method of preventing, treating or improving the effective treatment of MRSA by targeting a carotenoid. In one aspect, the carotenoid is a *Staphylococcus* sp. carotenoid. In another aspect, the method comprises targeting of the carotenoid comprises a carotenogenesis inhibitor. In yet a further embodiment, the carotenogenesis inhibitor is a mixed function oxidase inhibitor such as, for example, 2-diethylaminoethyl-2,2-diphenyl-valerate (SKF 525-A).

The invention also provides a method of screening for an MRSA therapeutic agent useful to treat a bacterial infection comprising contacting a bacteria that produces a carotenoid with a test agent suspected of inhibiting the production or activity of a carotenoid and measuring the effect of the agent in the presence and absence of an oxidative agent.

BRIEF DESCRIPTION OF THE FIGURES

FIG. 6A).

DETAILED DESCRIPTION

Figure 1:
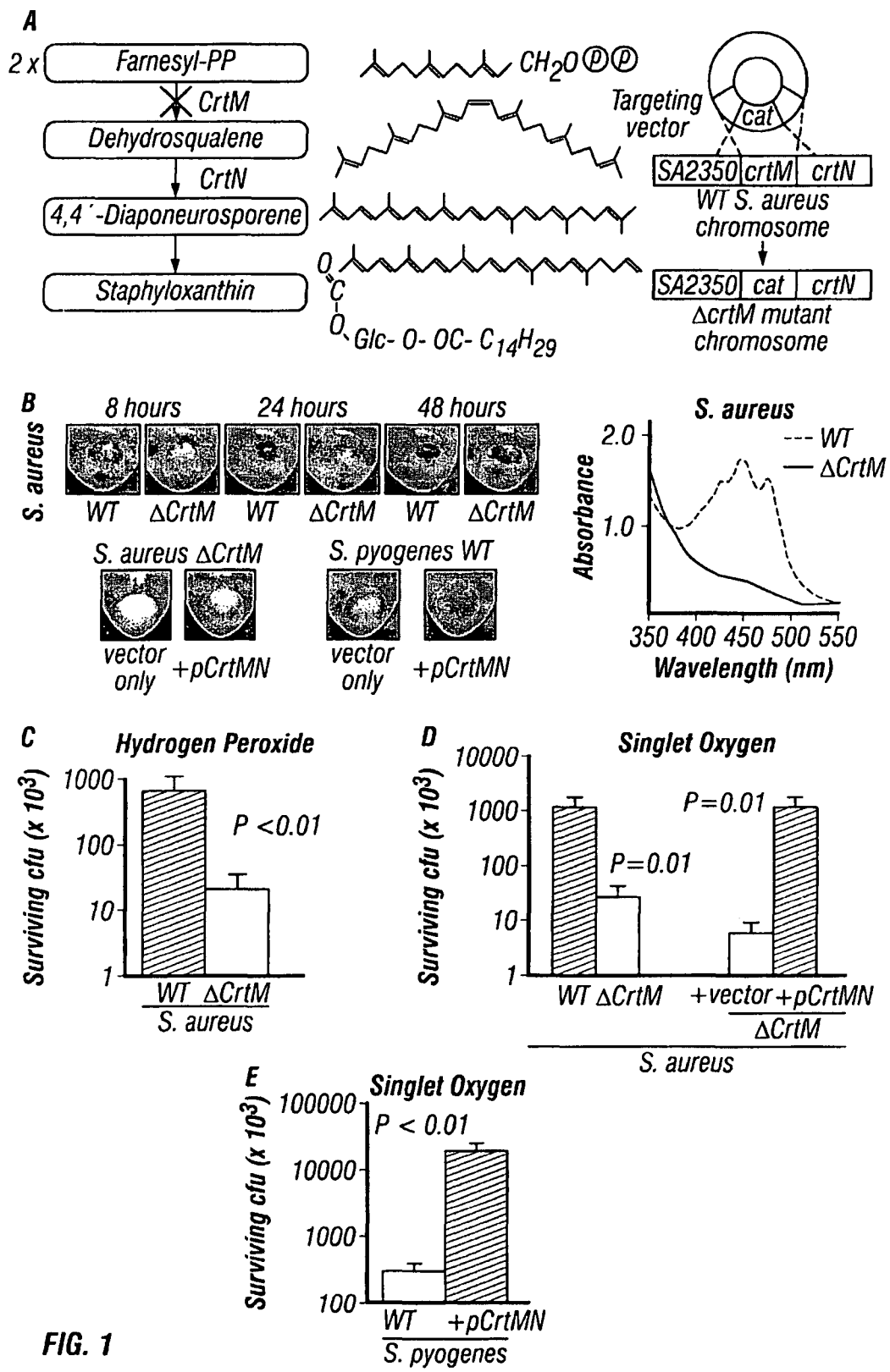
FIG. 1A-E shows a genetic manipulation of *Staphylococcus aureus* carotenoid pigment and its antioxidant function. A) Biochemical pathway for *S. aureus* carotenogenesis and mutagenesis of crtM (encoding dehydrosqualene synthase) by allelic replacement. B) Elimination of *S. aureus* pigmentation in ΔcrtM mutant; heterologous expression of *S. aureus* 4'4'-diaponeurosporene pigment in *Streptococcus pyogenes*. Increased susceptibility of the *S. aureus* ΔCrtM mutant to killing by C) hydrogen peroxide or D) singlet oxygen, with restoration of WT resistance levels upon complementation with pCrtMN. E) Decreased singlet oxygen susceptibility of *S. pyogenes* expressing 4'4'-diaponeurosporene. Error bars represent standard deviation of depicted variable; results shown are representative of at least three experiments.

As used herein and in the appended claims, the singular forms "a," "and," and "the" include plural referents unless the context clearly dictates otherwise. Thus, for example, reference to "a protein" includes a plurality of such proteins and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Methods and compositions useful for treatment of microbial infections, wherein the microbe expresses a carotenoid are provided. For example, methods and compositions useful for the treatment of *S. aureus* infections, including those produced by methicillin- and vancomycin-resistant strains, are provided by the invention. The methods and compositions of the invention can be used alone or in combination with traditional antimicrobials and antibiotics to treat such infections. In addition, the methods and compositions disclosed herein can be used in settings such as foreign-body, catheter or endovascular infections, chronic osteomyeletis, hospital acquired or post-operative infections, recurrent skin infections, or for *S. aureus* infections in the immunocompromised host.

Carotenoids represent a major class of natural pigments. More than 600 different carotenoids have been identified in bacteria, fungi, algae, plants and animals (Staub, O., In: Pfander, H. (ed.), Key to Carotenoids, $2^{nd}$ ed., Birkhuser Verlag, Basel). They function as accessory pigments in photosynthesis, as antioxidants, as precursors for vitamins in humans and animals and as pigments for light protection and species specific coloration. Carotenoids have historically been of interest, e.g., for pharmaceuticals, food colorants, and animal feed and nutrient supplements. The discovery that these natural products can play an important role in the prevention of cancer and chronic disease (mainly due to their antioxidant properties) and, more recently, that they exhibit significant tumor suppression activity due to specific interactions with cancer cells, has boosted interest in their pharmaceutical potential (Bertram, J. S., Nutr. Rev., 1999; 57:182-191; Singh, et al., Oncology, 1998; 12:1643-168; Rock, C. L., Pharmacol. Ther., 1997; 75:185-197; Edge, et al., J. Photochem. Photobiol., 1997; 41:189-200).

Carotenoid can be produced in recombinant microorganisms by combining biosynthetic genes from different organisms to create biosynthetic pathways. At present more than 150 genes for 24 carotenogenic enzymes (crt) have been isolated from bacteria, plants, algae and fungi that can be used to engineer a variety of diverse carotenoids.

Complete carotenoid biosynthesis pathways have been cloned from a number of bacteria, where the biosynthesis enzyme genes are arranged in gene cluster (reviewed in Armstrong, Ann. Rev. Microbiol., 1997, 51:629; Sandmann, Eur. J. Biochem., 1994, 223:7). The pathways Erwinia and Rhodobacter for the synthesis of zeaxanthin diglucoside and the acyclic xanthophylls speroidene and spheroidenone, respectively, were the first from which all involved enzymes have been identified (Armstrong et al., Mol. & General Gene., 1989, 216:254; Lang et al., J. Bacteriol., 1995, 177:2064; Lee and Liu, Mol. Microbiol., 1991, 5:217; Misawa et al., J. Bacteriol., 1990, 172:6704).

Various techniques have been applied for cloning of carotenogenic genes (Hirschberg, J., In: Carotenoids: Biosynthesis and Metabolism, Vol. 3, Carotenoids, G. Britton, Ed. Basel: Birkhuser Verlag, 148-194, 1998). Functional color complementation in *E. coli* expressing carotenogenic genes from Erwinia has been used successfully for the cloning of a variety of microbial and plant carotenogenic genes (Verdoes et al., Biotech. and Bioeng., 1999, 63:750; Zhu et al., Plant and Cell Physiology, 1997, 38:357; Kajiwara et al., Plant Mol. Biol., 1995, 29:343; Pecker et al., Plant Mol. Biol., 1996, 30:807; plant carotenoid biosynthesis is reviewed in Hirschberg et al., Pure and Applied Chemistry, 1997, 69:2151; Cunningham and Gantt, Ann. Rev. of Plant Physiol. and Plant Mol. Biol., 1998, 49:557).

Genes encoding the early carotenoid biosynthesis enzymes GGDP synthase, phytoene synthase and phytoene desaturase account for more than half of all cloned carotenogenic genes. Different phytoene desaturase genes are available that introduce two, three, four or five double bonds into phytoene to produce carotene (plant, cyanobacteria, algae) (Bartley et al., Eur. J. of Biochem., 1999, 259:396), neurosporene (Rhodobacter) (Raisig et al., J. Biochem., 1996, 119:559), lycopene (most eubacteria and fungi) (Verdoes, et al., Biotech. and Bioeng., 1999, 63:750; RuizHidalgo et al., Mol. & Gen. Genetics, 1997, 253:734) or 3,4-didehydrolycopene (*Neurospora crassa*) (Schmidhauser et al., Mol. and Cell Biol., 1990, 10:5064), respectively. The following are examples of carotenoid biosynthesis genes have been cloned:

crtE: GGPP-synthase from *R. capsulatus* and *E. uredovora*
crtB: phytoene synthase from *R. capsulatus* and *E. uredovora*
crtI: phytoene desaturase from *E. uredovora* and *E. herbicola*
crtY: lycopene cyclase from *E. uredevora* and *E. herbicola*
crtA: spheroidene monooxygenase from *R. capsulatus* and *R. spaeroides*
crtO: β-C4-ketolase (oxygenase) from *Synechocistis* sp.
crtW: β-C4-ketolase from *Algaligenes* sp., *A. aurantiacum*
crtD: methoxyneurosporene desaturase from *R. capsulatus* and *R. spaeroides*
crtX: zeaxanthin glucosyl transferase from *E. uredovora* and *E. herbicola*
crtZ: β-carotene hydroxylase from *E. uredovora* and *E. herbicola*
crtU: β-carotene desaturase from *S. griseus*
crtM: dehydrosqualene synthase from *S. aureus*
crtN: dehydrosqualene desaturase from *S. aureus*.

A leading human pathogen *Staphylococcus aureus* (*S. aureus*) was named secondary to it characteristic golden yellow pigmentation (aureus=golden, Latin) in comparison to less virulent staphylococci (e.g. *S. epidermidis*) that normally colonize the skin surface. Subsequent research regarding the *S. aureus* pigment unraveled an elaborate biosynthetic pathway that produces a series of carotenoids. Similar carotenoids produced in dietary fruits and vegetables are well recognized as potent antioxidants by virtue of their free radical scavenging properties and exceptional ability to quench singlet oxygen. The *S. aureus* pigment may have similar properties. The invention examined whether *S. aureus* could utilize its golden carotenoid pigment to resist oxidant based clearance mechanisms of the host innate immune system. For example, neutrophils and macrophages kill bacteria by generating an "oxidative burst" of reactive molecules such as peroxide, bleach and singlet oxygen that kill bacteria that they have phagocytosed.

Golden color imparted by carotenoid pigments is the eponymous feature of the human pathogen *Staphylococcus aureus*. A molecular genetic analysis pairing mutagenesis and heterologous expression was used to show that this hallmark phenotype is in fact a virulence factor, serving to protect the bacterium from phagocytic killing through its antioxidant properties. In the present era, effective control of this important disease agent is compromised by rapid evolution of antimicrobial resistance in both community and hospital settings. The invention demonstrates that the inhibition of carotenogenesis offers a novel therapeutic approach to the treatment of complicated *S. aureus* infections, effectively rendering the pathogen more susceptible to clearance by normal host innate immune defenses.

The invention demonstrates that carotenoid pigment production contributes to resistance of Group B *Streptococcus* (GBS) to macrophage killing. GBS is the leading cause of invasive bacterial infections such as pneumonia, sepsis and meningitis in human neonates. A gene required for production of carotenoid pigment (CylE) has been identified. The pigment is required for the organism's production of a hemolysin/cytolysin toxin that have cell damaging and proinflammatory properties important in disease pathogenesis. Other bacterial and fungal human pathogens associated with invasive infections produce carotenoid or melanin-like pigments with antioxidant properties (e.g. *Aspergillus fumigatus, Burkholderia cepacia, Serratia marcesens*), suggesting a common pathogenic theme and revealing a potential selective advantage for pigment production against phagocytic clearance mechanisms.

Accordingly, the approach of targeting pigment production for antimicrobial therapy can be extended to organisms that produce pigments (e.g., carotenoid pigments or other pigments that confer oxidative protection). In particular, *Aspergillus* sp. are an important cause of mortality in immunocompromised subjects (e.g., cancer chemotherapy) and *Burkholderia cepacia* is an important cause of mortality in cystic fibrosis. Both *Aspergillus* and *Burkholderia* are commonly multidrug resistant and recalcitrant to existing antibiotic therapies.

The invention demonstrates that by using a molecular genetic approach of targeted gene deletion (to create nonpigmented *S. aureus* mutants) and cloning techniques (to express the *S. aureus* pigment in other bacteria) to create "living reagents" the true importance of the pigment in *S. aureus* disease pathogenesis was identified. *S. aureus* carotenoid pigment did indeed protect the bacterium against peroxide and singlet oxygen and made it more resistant to killing in mouse and human blood and by purified human neutrophils. Using a mouse model of *S. aureus* abscess formation, it was demonstrated the carotenoid pigment promoted bacterial survival and disease progression in vivo. Control experiments using mice impaired in neutrophil oxidant production showed that carotenoid pigment production contributed to *S. aureus* virulence by virtue of its antioxidant properties. The invention demonstrates that pharmacological inhibition of *S. aureus* pigment production rendered the bacterium more susceptible to oxidants and impaired in blood survival.

One important mechanism by which phagocytic cells eliminate pathogens is through release of reactive oxygen species generated by NADPH oxidase. The invention demonstrates that carotenoids such as those expressed by *S. aureus* serve a protective function against these defense molecules. For example, a ΔCrtM mutant was killed 10 to 100-fold more efficiently by hydrogen peroxide and 100 to 1,000-fold more efficiently by singlet oxygen than the WT *S. aureus* strain. Similarly, heterologous expression of staphylococcal pigment in *S. pyogenes* was associated with a 100 to 1,000-fold decrease in singlet oxygen lethality.

The invention provides methods and agents that inhibited carotenogenesis for the treatment of microbial infections and to facilitate anti-microbial activity. For example, in one aspect, the mixed function oxidase inhibitor 2-diethylaminoethyl-2,2-diphenyl-valerate (SKF 525-A, Calbiochem) is shown to inhibit pigment formation in *S. aureus*, and a dose-dependent decrease in carotenoid production was demonstrated in the WT strain of *S. aureus* grown in the presence of the agent. Blocking *S. aureus* pigment formation led to a commensurate dose-dependent increase in the susceptibility of the organism to singlet oxygen killing and a decrease in its ability to survive in human whole blood. As a control, the ΔCrtM mutant was exposed to SKF 525-A in parallel experiments with no significant effects on oxidant susceptibility or blood survival.

The invention provides methods and compositions useful for treating bacterial infection by inhibiting the production and/or activity of carotenoids. More particularly, the invention provides methods of treating a subject having a bacterial infection (e.g., a bacterial infection of *Staphylococcus* sp.) comprising contacting a subject with an agent that inhibits the activity and/or production of a carotenoid of the *Staphylococcus* sp. In one aspect, the agent is a small molecule, a polynucleotide (e.g., a ribozyme or antisense molecule), a polypeptide (e.g., an antibody) or a peptidomimetic. In one aspect of the invention, the agent is a pharmacologic agent that inhibits carotenogenesis. For example, the agent can be a mixed function oxidase inhibitor such as 2-diethylaminoethyl-2,2-diphenyl-valerate (SKF 525-A, Calbiochem), 2,4-dichloro-6-phenylphenoxyethylamine, 2,4-dichloro-6-phenylphenoxyethyldiethylamine, and piperonyl butoxide.

In another aspect, the carotenogenesis inhibitor comprises a oligonucleotide or polynucleotide (e.g., an antisense, ribozyme, or siRNA). For example, antisense technology is a method of down-regulating genes where the sequence of the target gene is known. A large number of carotenoid genes are known in the art including those of *Staphylococcus* sp. In this aspect, a nucleic acid segment from the desired gene (e.g., crtM and/or crtN) is cloned and operably linked to a promoter such that the anti-sense strand of RNA will be transcribed. This construct is then introduced into a target cell and the antisense strand of RNA is produced. Antisense RNA inhibits gene expression by preventing the accumulation of mRNA encoding the protein of interest. Thus, an antisense molecule against crtM and/or crtN will result in the reduction of synthesis of carotenoids a pathogenic microbe, thereby rendering the microbe susceptible to oxidative damage by phagocytes. A person skilled in the art will know that certain considerations are associated with the use of antisense technologies in order to reduce expression of particular genes. For example, the proper level of expression of antisense genes may require the use of different chimeric genes utilizing different regulatory elements known to the skilled artisan.

Within the context of the invention, it is apparent that modulating the expression of bacterial carotenoid biosynthetic pathways by the use of inhibitory nucleic acids provides a useful therapeutic method. For example, the invention identifies a number of genes encoding enzymes in the carotenoid biosynthetic pathway including crtM and crtN. Alternatively (or in addition to), it may be desirable to knockout the crtM/crtN genes leading to the synthesis of $C_{30}$ carotenoids. Common molecular biology techniques can be used to generate inhibitory nucleic acid molecules such as, for example, antisense molecules that can interact with a crtN and/or M nucleic acid produced by wild type bacteria (e.g., *Staphylococcus* sp.).

As used herein an isolated nucleic acid is substantially free of proteins, lipids, and other nucleic acids with which an in vivo-produced nucleic acids naturally associated. Typically, the nucleic acid is at least 70%, 80%, 90% or more pure by weight, and conventional methods for synthesizing nucleic acids in vitro can be used in lieu of in vivo methods. As used herein, "nucleic acid" or "polynucleotide" or "oligonucleotide" refers to a polymer of deoxyribonucleotides or ribonucleotides, in the form of a separate fragment or as a component of a larger genetic construct (e.g., by operably linking a promoter to a nucleic acid encoding, for example, an antisense molecule). Numerous genetic constructs (e.g., plasmids and other expression vectors) are known in the art and can be used to produce a desired nucleic acid of the disclosure in cell-free systems or prokaryotic or eukaryotic (e.g., yeast, insect, or mammalian) cells. The nucleic acids of the disclosure can readily be used in conventional molecular biology methods to produce the peptides of the disclosure.

Polynucleotides comprising an antisense nucleic acid, ribozyme, or siRNA can be inserted into an "expression vector." The term "expression vector" refers to a genetic construct such as a plasmid, virus or other vehicle known in the art that can be engineered to contain, for example, an antisense molecule. The expression vector typically contains an origin of replication, and a promoter, as well as genes that allow phenotypic selection of the transformed cells. Various promoters, including inducible and constitutive promoters, can be utilized in the disclosure. Typically, the expression vector contains a replicon site and control sequences that are derived from a species compatible with the host/target cell.

Transformation or transfection of a host/target cell with a polynucleotide of the disclosure can be carried out using conventional techniques known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

A host cell or target cell encompassed by of the disclosure are any cells in which the polynucleotides of the disclosure can be used to express an inhibitory nucleic acid molecule. The term also includes any progeny of a host/target cell. Host/target cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as Drosophila S2 and *Spodoptera* Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004-2012, 1996; Kaufman et al., J. Biol Chem 263: 6352-6362, 1988; McKinnon et al., J Mol Endocrinol 6:231-239, 1991; Wood et al., J. Immunol 145:3011-3016, 1990). The dihydrofolate reductase (DHFR)-deficient mutant cell lines (Urlaub et al., Proc Natl Acad Sci USA 77:4216-4220, 1980) are the CHO host cell lines commonly used because the efficient DHFR selectable and amplifiable gene expression system allows high level recombinant protein expression in these cells (Kaufman, Meth Enzymol 185:527-566, 1990). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

The activity of such inhibitory agents (e.g., small molecules (2-diethylaminoethyl-2,2-diphenyl-valerate) and inhibitory nucleic acids) can be determined using conventional methods known to those of skill in the art, such as the assays described herein (both in vitro and in vivo assays).

The disclosure also provides a method for inhibiting the growth of a bacterium by contacting the bacterium with an inhibiting effective amount of a carotenoid biosynthesis inhibitor (i.e., a carotenogenesis inhibitor). The term "contacting" refers to exposing the microbe (e.g., bacterium) to an agent so that the agent can inhibit, kill, or lyse microbe or render it susceptible to oxidative destruction. Contacting of an organism with an agent that inhibits carotenoid biosynthesis can occur in vitro, for example, by adding the agent to a bacterial culture, or contacting a bacterially contaminated surface with the agent.

Alternatively, contacting can occur in vivo, for example by administering the agent to a subject afflicted with a bacterial infection or susceptible to infection. In vivo contacting includes both parenteral as well as topical. "Inhibiting" or "inhibiting effective amount" refers to the amount of agent that is sufficient to cause, for example, a bacteriostatic or bactericidal effect, reduce coloration of a particular bacterial cell type, or decrease the amount of a particular carotenoid produced by the bacteria. Bacteria that can be affected by the use of a carotenoid inhibitor include both gram-negative and gram-positive bacteria. For example, bacteria that can be affected include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter* species, *Proteus mirablis* and other sp., *Pseudomonas aeruginosa, Klebsiella pneumoniae, Salmonella, Shigella, Serratia*, and *Campylobacter jejuni*. In particular the methods and compositions of the invention are useful against any pathogen that synthesizes a carotenoid the confers protection against reactive oxygen species (e.g., species produced by NADPH oxidase). Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. The method for inhibiting the growth of bacteria can also include contacting the bacterium with the peptide in combination with one or more antibiotics.

Fungal organisms may also be affected by the carotenoid inhibitors (e.g., *Microsporum canis* and other *Microsporum* sp.; and *Trichophyton* sp. such as *T. rubrum*, and *T. mentagrophytes*), yeasts (e.g., *Candida albicans, C. Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., *Zygomycetes* (e.g., *Rhizopus, Mucor*), *Paracoccidioides brasiliensis, Blastomyces dermatitides, Histoplasma capsulatum, Coccidioides immitis*, and *Sporothrix schenckii*.

A carotenoid biosynthesis inhibitor can be administered to any host, including a human or non-human animal, in an amount effective to inhibit the production of carotenoids that confer, for example, resistance to oxidative attack. In one aspect, the administration results in the inhibition of growth of a bacterium, virus, and/or fungus. Thus, the methods and compositions are useful as antimicrobial agents, antiviral agents, and/or antifungal agents.

Any of a variety of art-known methods can be used to administer a carotenoid inhibitory agent either alone or in combination with other antibiotic agents. For example, administration can be parenterally by injection or by gradual infusion over time. The agent(s) can be administered intravenously, intraperitoneally, intramuscularly, subcutaneously, intracavity, by inhalation, or transdermally.

In another aspect, a carotenoid biosynthesis inhibitor can be formulated either alone or in combination with other antibiotics/antifungals for topical administration (e.g., as a lotion, cream, spray, gel, or ointment). Such topical formulations are useful in treating or inhibiting microbial, fungal, and/or viral presence or infections on the eye, skin, and mucous membranes such as mouth, vagina and the like. Examples of formulations in the market place include topical lotions, creams, soaps, wipes, and the like. It may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a composition comprising a carotenoid inhibitor include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

The disclosure provides a method for inhibiting a bacterial, viral and/or fungal-associated disorder by contacting or administering a therapeutically effective amount of a carotenoid biosynthesis inhibitor (e.g., a crtM and/or crtN inhibitor) either alone or in combination with other antimicrobial agents to a subject who has, or is at risk of having, such a disorder. The term "inhibiting" means preventing or ameliorating a sign or symptoms of a disorder (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, adult respiratory distress syndrome, shock, and organ failure. Examples of subjects who can be treated in the disclosure include those at risk for, or those suffering from, a toxemia, such as endotoxemia resulting from a gram-negative bacterial infection, venom poisoning, or hepatic failure. Other examples include subjects having a dermatitis as well as those having skin infections or injuries subject to infection with gram-positive or gram-negative bacteria, a virus, or a fungus. Examples of candidate subjects include those suffering from infection by E. coli, Neisseria meningitides, staphylococci, or pneumococci. Other subjects include those suffering from gunshot wounds, renal or hepatic failure, trauma, burns, immunocompromising infections (e.g., HIV infections), hematopoietic neoplasias, multiple myeloma, Castleman's disease or cardiac myxoma. Those skilled in the art of medicine can readily employ conventional criteria to identify appropriate subjects for treatment in accordance with the disclosure.

A therapeutically effective amount can be measured as the amount sufficient to decrease a subject's symptoms of dermatitis or rash by measuring the frequency of severity of skin sores. Typically, the subject is treated with an amount of a therapeutic composition of the invention sufficient to reduce a symptom of a disease or disorder by at least 50%, 90% or 100%. Generally, the optimal dosage will depend upon the disorder and factors such as the weight of the subject, the type of bacteria, virus or fungal infection, the weight, sex, and degree of symptoms. Nonetheless, suitable dosages can readily be determined by one skilled in the art. Typically, a suitable dosage is 0.5 to 40 mg/kg body weight, e.g., 1 to 8 mg/kg body weight.

As mentioned previously, the compositions and methods of the invention can include the use of additional (e.g., in addition to a carotenoid biosynthesis inhibitor) therapeutic agents (e.g., an inhibitor of TNF, an antibiotic, and the like). The carotenoid biosynthesis inhibitor, other therapeutic agent(s), and/or antibiotic(s) can be administered, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal, antiviral and/or antifungal amount.

The methods and compositions of the invention utilizing carotenoid biosynthesis inhibitors are useful as a broad-spectrum antimicrobials suitable for tackling the growing problem of antibiotic-resistant bacteria strains, and for treating and/or preventing outbreaks of infectious diseases, including diseases caused by bioterrorism agents like anthrax, plague, cholera, gastroenteritis, multidrug-resistant tuberculosis (MDR TB).

A pharmaceutical composition comprising a carotenogenesis inhibitor according to the disclosure can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. A "therapeutically effective dose" is the quantity of an agent according to the disclosure necessary to prevent, to cure, or at least partially arrest the symptoms of a bacterial infection. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of infections. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

An agent useful to inhibit carotenogenesis in a bacterial organism (e.g., *Staphylococcus* sp.) maybe used in combination with commonly used antibiotics and/or antimicrobials. Accordingly, a pharmaceutical composition of the invention can comprise a carotenogenesis inhibitor and one or more additional antimicrobials or antibiotics.

The following example(s) are provided in illustration of the invention and should not be construed in any way as constituting a limitation thereof.

EXAMPLES

The biosynthetic pathway for *S. aureus* carotenoids includes the essential functions of genes crtM and crtN, encoding dehydrosqualene synthase and dehydrosqualene desaturase, respectively. To probe the biological activities of the *S. aureus* pigment, an isogenic mutant of a golden-colored human clinical isolate by allelic replacement of crtM was generated. The ΔCrtM mutant was nonpigmented and lacked the characteristic triple-peak spectral profile of wild-type carotenoid at 440, 462 and 491 nM wavelengths. No differences in growth rate, stationary phase density, surface charge, buoyancy or hydrophobicity were observed between WT and ΔCrtM *S. aureus*. *S. aureus* crtM and crtN together are sufficient for production of 4,4'-diaponeurosporene. To facilitate gain of function analyses, both genes were expressed in the nonpigmented *Streptococcus pyogenes*, a human pathogen associated with a disease spectrum similar to that of S. aureus. When transformed with a pCrtMN plasmid, S. pyogenes gained yellow pigmentation with the spectral characteristics of a carotenoid. Complementation of the S. aureus ΔCrtM mutant with the same pCrtMN vector also partially restored pigmentation.

Bacteria, Mice, Human CGD Patient and Chemical Reagents:

Wild-type S. aureus strain (Pig1), isolated from the skin of a child with atopic dermatitis. Streptococcus pyogenes strain 5448 is a well-characterized serotype M1T1 clinical isolate[18]. CD1 and C57Bl/6 mice were purchased from Charles River. The gp91$^{Phox-/-}$ mice were bred at the Veteran's Administration Medical Center, San Diego and maintained on trimethoprim/sulfamethoxazole prophylaxis until 3 d prior to experiments. S. aureus and S. pyogenes were propagated in Todd-Hewitt broth (THB) or on THB agar (Difco, Detroit, Mich.). Unless otherwise indicated, all experiments were performed with bacteria derived from S. aureus 36-48 h stationary phase cultures or S. pyogenes 24 h stationary phase cultures, a point when pigmentation phenotypes were readily apparent.

Human CGD Patient:

The patient was an 18 y.o. female with a gp47$^{phox}$ deficiency (homozygous ΔGT deletion in exon 2). At the time of study she was in good health and her only medication was interferon-γ (50 mcg/m$^2$) administered three times weekly by subcutaneous injection.

Generation of the Carotenoid-Deficient S. aureus Mutant, ΔCrtM.

Precise, in-frame allelic replacement of the S. aureus crtM gene with a chloramphenicol acetyltransferase (cat) cassette was performed using PCR-based methods as described for S. pyogenes[19] or Streptococcus agalactiae[20], with minor modifications. Primers were designed based on the published S. aureus crtMN sequence[6] cross-referenced to genome S. aureus strain N315[21]. PCR was used to amplify ~500 bp upstream of crtM with primers crtMupF 5'-TTAGGAAGTG-CATATACTTCAC-3' (SEQ ID NO:1) and crtMstartR 5'-GGTGGTATATCCAGTGATTTTTTTCTC-CATACTAGTCCTCCTATATTGAAATG-3' (SEQ ID NO:2), along with approximately 500 bp of sequence immediately downstream of crtM with primers crtMendF 5'-TACT-GCGATGAGTGGCAGGGCGGGGCGTAA-CAAAGTATTTAGTATTGAAGC-3' (SEQ ID NO:3) and crtMdownR 5'-GGCACCGTTATACGATCATCGT-3' (SEQ ID NO:4). The crtMstartR and crtMendF primers were constructed with 25 bp 5' extensions corresponding to the 5' and 3' ends of the cat gene, respectively. The upstream and downstream PCR products were then combined with a 650 bp amplicon of the complete cat gene (from pACYC184) as templates in a second round of PCR using primers crtMupF and crtMdownR. The resultant PCR amplicon, containing an in-frame substitution of crtM with cat, was subcloned into temperature-sensitive vector pHY304 to create the knockout plasmid. This vector was transformed initially into permissive S. aureus strain RN4220 (provided by Dr. Paul Sullam) and then into S. aureus strain Pig1 by electroporation. Transformants were grown at 30° C., shifted to the nonpermissive temperature for plasmid replication (40° C.), and differential antibiotic selection and pigment phenotype were used to identify candidate mutants. Allelic replacement of the crtM allele in was confirmed unambiguously by PCR reactions documenting targeted insertion of cat and absence of crtM in chromosomal DNA isolated from the final mutant ΔCrtM.

Complementation and Heterologous Expression Studies.

Primers CrtF 5'-CAGTCTAGAAATGGCATTTCAATAT-AGGAG-3' (SEQ ID NO:5) and CrtR 5'-ATCGAGATCTCT-CACATCTTTCTCTTAGAC-3' (SEQ ID NO:6) were used to amplify the contiguous CrtM and CrtN genes from the chromosome of WT S. aureus strain Pig1. The fragment was directionally cloned into the shuttle expression vector pDCerm[19] and the recombinant plasmid (pCrtMN) used to transform by electroporation the S. aureus ΔCrtM mutant and S. pyogenes strain 5448.

Spectral Profile of the S. aureus Carotenoid.

Stationary phase (48 h) cultures of WT S. aureus Pig1 and its isogenic ΔCrtM mutant were subjected to methanol extraction. The absorbance profile of the extracts was measured with a MBA 2000 spectrophotometer (Perkin Elmer).

Oxidant Susceptibility Assays.

Tests for susceptibility to oxidants were performed either in PBS (S. aureus) or THB (S. pyogenes). Hydrogen peroxide ($H_2O_2$) was added to 1.5% final concentration, $2\times10^9$ bacteria incubated at 37° C. for 1 h, then 1,000 U/ml of catalase (Sigma) added to quench residual $H_2O_2$. Dilutions were plated on THA for enumeration of surviving cfu. For the singlet oxygen assay, $10^8$ S. aureus or $4\times10^8$ S. pyogenes were incubated at 37° C. in individual wells of a 24-well culture plate in the presence or absence of 1-6 µg/ml methylene blue and situated exactly 10 cm from a 100-watt light source. Bacterial viability was assessed after 1-3 h by plating dilutions on THA. Control plates handled identically but wrapped in foil or exposed to light in the absence of methylene blue did not show evidence of bacterial killing.

Whole Blood Killing Assays.

Bacteria were washed twice in PBS, diluted to an inoculum of $10^4$ cfu in 25 µl PBS, and mixed with 75 µl of freshly drawn human or mouse blood in heparinized tubes. The tubes were incubated at 37° C. for 4 h with agitation, at which time dilutions were plated on THA for enumeration of surviving cfu.

Neutrophil Intracellular Survival Assay.

Neutrophils were purified from healthy human volunteers using a Histopaque gradient (Sigma) per manufacturer's directions. Intracellular survival assays were performed as follows. Bacterial cultures were washed twice in PBS, diluted to a concentration of $4.5\times10^6$ cfu in 100 µl RPMI+10% FCS, and mixed with $3\times10^5$ neutrophils in the same media (multiplicity of infection, MOI=15:1), centrifuged at 700×g for 5 min, then incubated at 37° C. in a 5% $CO_2$ incubator. Gentamicin (Gibco) (final concentration 400 µg/ml for S. aureus and 100 µg/ml for S. pyogenes) was added after 10 min to kill extracellular bacteria. At specified time points, the contents of sample wells were withdrawn, centrifuged to pellet the neutrophils, and washed to remove the antibiotic medium. Neutrophils were then lysed in 0.02% triton-X, and cfu calculated by plating on THA. Several assays were repeated with addition of a step involving preincubation of the bacterial inoculum with 10% autologous human serum for 15 min on ice.

Murine Model of Subcutaneous Infection.

Ten to 16 week old CD-1 or gp91$^{Phox-/-}$ mice were injected subcutaneously in one flank (chosen randomly) with the bacterial test strain, and simultaneously in the opposite flank with a different strain for direct comparison. Bacterial cultures were washed, diluted and resuspended in PBS mixed 1:1 with sterile Cytodex beads (Amersham) at the specified inoculum, following an established protocol for generating localized S. aureus and S. pyogenes subcutaneous infection. Lesion size, as assessed by the maximal length×width of the developing ulcers, was recorded daily. Cumulative lesion size represents the total sum of lesion sizes from all animals in each treatment group on a given day. At day 8 (S. aureus) or day 5 (S.

*pyogenes*), animals were euthanized, skin lesions excised, homogenized in PBS, and plated on THA for quantitative culture.

Statistics.

The significance of experimental differences in oxidant sensitivity, blood killing, and neutrophil survival were evaluated by unpaired Students t test. Results of the mouse in vivo challenge studies were evaluated by paired Student's t test.

Assurances.

All animal experiments were approved by the UCSD Committee on the Use and Care of Animals and performed using accepted veterinary standards. Experimentations using human blood were approved by the Dual Tracked UCSD Human Research Protection Program/CHSD IRB. Prior informed consents were obtained from the human subjects.

Assays for Buoyancy, Surface Charge, and Hydrophobicity.

To measure buoyancy, sequential overlay gradients of 1 ml each 70%, 60% and 50% Percoll were prepared in 5 ml glass test tubes. One ml of overnight bacterial culture was placed on top of the Percoll layers, the tubes centrifuged in a swinging bucket centrifuge for 8 min at 500×g, and the migration of bacteria to various Percoll interphases recorded. To measure surface charge, bacteria were harvested by centrifugation and washed in morpholinepropanesulfonic acid (MOPS) buffer (20 mM, pH=7.0). One ml of culture was resuspended in 0.5 ml MOPS and the OD600 measured. Bacteria cells were incubated at room temperature or 15 min with cytochrome C (Sigma, St. Louis, Mo.) at a final concentration of 0.5 mg/ml. Samples were centrifuged (13,000×g for 5 min) and the amount of cytochrome C remaining in the supernatant quantitated at 530 nm. Cytochrome C values were adjusted to reflect binding per culture $OD_{600}$=1.0. To measure hydrophobicity, 0.5 ml of *S. aureus* culture was washed and resuspended in 1.0 ml PBS, 300 µl of n-hexadecane layered on top of the cell suspension, and tubes vortexed for 60 sec. Samples were incubated at RT for 30 min to allow for phase separation. The aqueous phase was removed and the ratio of the $OD_{600}$ of the aqueous phase versus the $OD_{600}$ of the culture in PBS determined.

Protease and Cathelicidin Sensitivity Assays.

Human neutrophil elastase, and cathepsin G were purchased from Calbiochem. The antimicrobial peptide mCRAMP was synthesized at the Louisiana State University Protein Facility (Martha Juban, Director). *S. aureus* cultures were diluted (1:2,000) in 10 mM phosphate buffer (pH 7.2)+ 0.5% LB to 1×10⁶ CFU/ml. Ninety µl of this bacterial suspension was added to replicate wells in a 96-well plate. Dilutions of the cathepsin G (20 and 100 mU/ml), human neutrophil elastase (12.5 and 50 µg/ml), and murine CRAMP (0.4-3 µM) were prepared in 10 mM phosphate buffer and added to wells in 10 µl volume; 10 mM phosphate buffer alone was used as a negative control. After 2 h incubation at 37° C., 25 µl aliquots of each well were serially diluted in PBS and plated on THB. Each experiment was performed in duplicate and repeated.

Phagocytotic Uptake Assay.

*S. aureus* were labeled with SYTOR9, a component of BacLight™ kit (Invitrogen, Carlsbad, Calif.), for 15 min at RT per manufacturer's guidelines. Labeled bacteria were washed×3 times to remove excess dye, then preopsonized in 10% autologous human serum for 10 min on ice. Bacteria were added to 3×10⁶ purified human neutrophils at MOI=15, incubated at 37° C. for 5 min, then centrifuged at 500×g for 6 min to pellet neutrophils. The supernatant was discarded and the cell pellet resuspended in 15 ml of 0.1 mg/ml ethidium bromide in PBS to quench fluorescence of extracellular bacteria. The percentage of neutrophils with intracellular bacteria was enumerated by direct visualization under fluorescent microscopy. Experiments were performed in duplicate and repeated. Representative images were captured on using Delta Vision Deconvolution Microscope System (Nikon TE-200 Microscope) at the UCSD Digital Imaging Core Facility.

The biosynthetic pathway for *S. aureus* carotenoids[6] includes the essential functions of genes crtM and crtN, encoding dehydrosqualene synthase and dehydrosqualene desaturase, respectively (FIG. 1a). To probe the biological activities of the *S. aureus* pigment, an isogenic mutant of a golden-colored human clinical isolate by allelic replacement of crtM was generated (FIG. 1a). Consistent with previous reports, pigmentation of the wild-type (WT) strain became apparent in early stationary phase of growth and continued to intensify before reaching a plateau at 36-48 h (FIG. 1b). The ΔCrtM mutant was nonpigmented and lacked the characteristic triple-peak spectral profile of wild-type carotenoid at 440, 462 and 491 nM wavelengths (FIG. 1b). No differences in growth rate, stationary phase density, surface charge, buoyancy or hydrophobicity were observed between WT and ΔCrtM *S. aureus* (FIGS. 5a-d). *S. aureus* crtM and crtN together are sufficient for production of 4,4'-diaponeurosporene[3]. To facilitate gain of function analyses, both genes were expressed in the nonpigmented *Streptococcus pyogenes*, a human pathogen associated with a disease spectrum similar to that of *S. aureus*. When transformed with the pCrtMN plasmid, *S. pyogenes* gained yellow pigmentation (FIG. 1b) with the spectral characteristics of a carotenoid. Complementation of the *S. aureus* ΔCrtM mutant with pCrtMN vector also fully restored pigmentation (FIG. 1b).

One important mechanism by which phagocytic cells eliminate pathogens is through release of reactive oxygen species generated by NADPH oxidase[7]. It has been suggested that bacterial carotenoids such as those expressed by *S. aureus* could serve a protective function against these defense molecules[8,9,10]. To test this experimentally, the susceptibility of WT and ΔCrtM *S. aureus* to oxidants in vitro was compared. As shown in FIGS. 1c and 1d, the ΔCrtM mutant was killed more efficiently by hydrogen peroxide and singlet oxygen compared to the WT *S. aureus* strain. Complementation with pCrtMN restored the ability of the ΔCrtM mutant to resist singlet oxygen killing (FIG. 1d). Similarly, heterologous expression of staphylococcal pigment in *S. pyogenes* led to a significant decrease in susceptibility to singlet oxygen (FIG. 1e).

Figure 2:
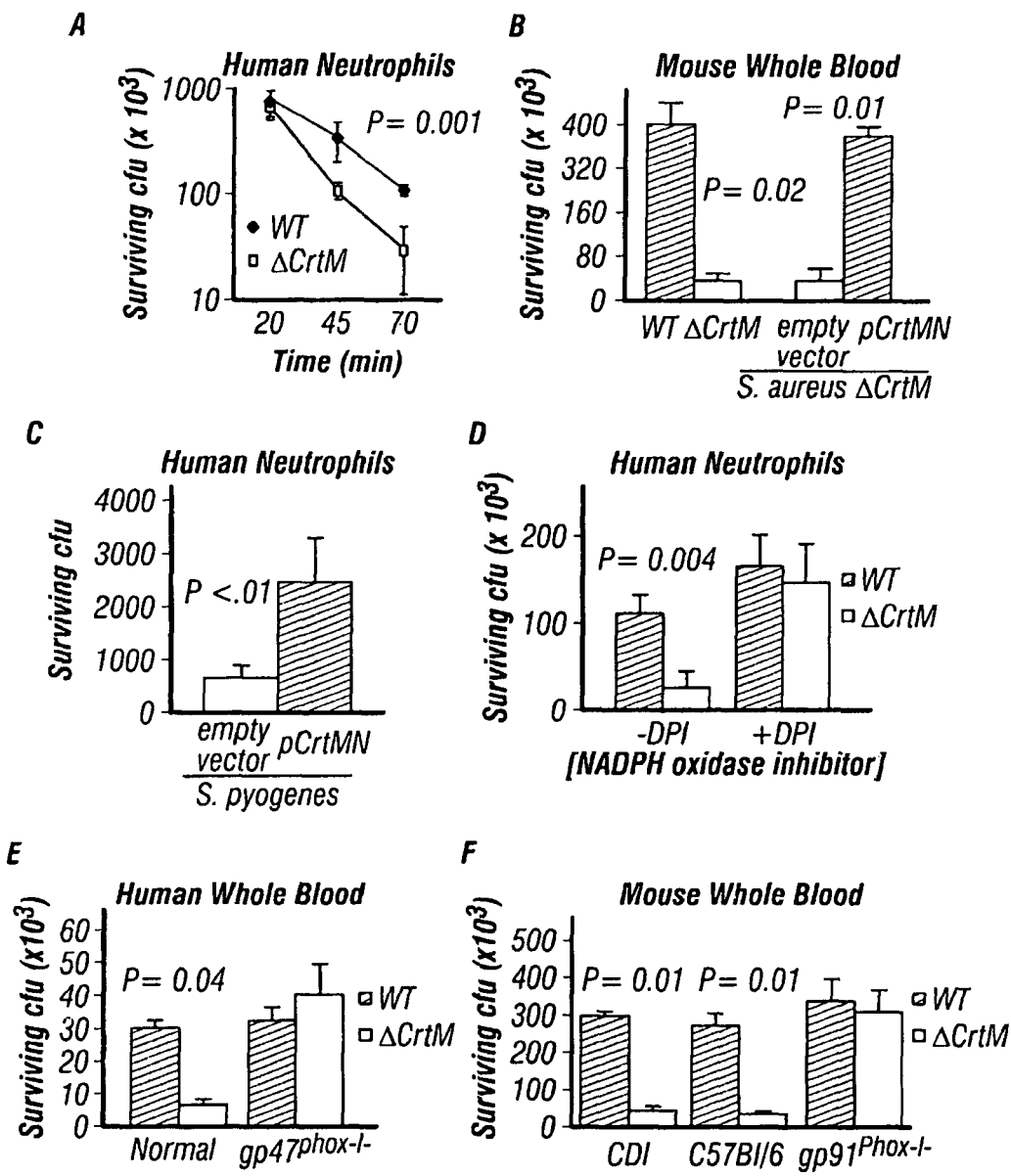
FIG. 2A-F shows *Staphylococcus aureus* carotenoid pigment confers resistance to oxidant killing in neutrophils and whole blood. Survival of WT and ΔCrtM *S. aureus* in A) coculture with isolated human neutrophils and B) murine whole blood. Also shown in (B) is whole blood survival of ΔCrtM complemented with vector alone or pCrtMN. (C) Effect of plasmid expression of crtMN on survival of *Streptococcus pyogenes* in mouse whole blood. D) Effect of oxidative burst inhibitor DPI on survival of WT and ΔCrtM mutant *S. aureus* human neutrophil coculture. Relative survival of WT and ΔCrtM mutant *S. aureus* in E) normal and $gp47^{phox-/-}$ patient lacking NADPH oxidase function or F) the blood of wild-type CD1 and C57Bl/6 mice and $gp91^{Phox-/-}$ mice. Results representative of at least three experiments. The assay using blood from the CGD human patient was performed twice.
Figure 6:
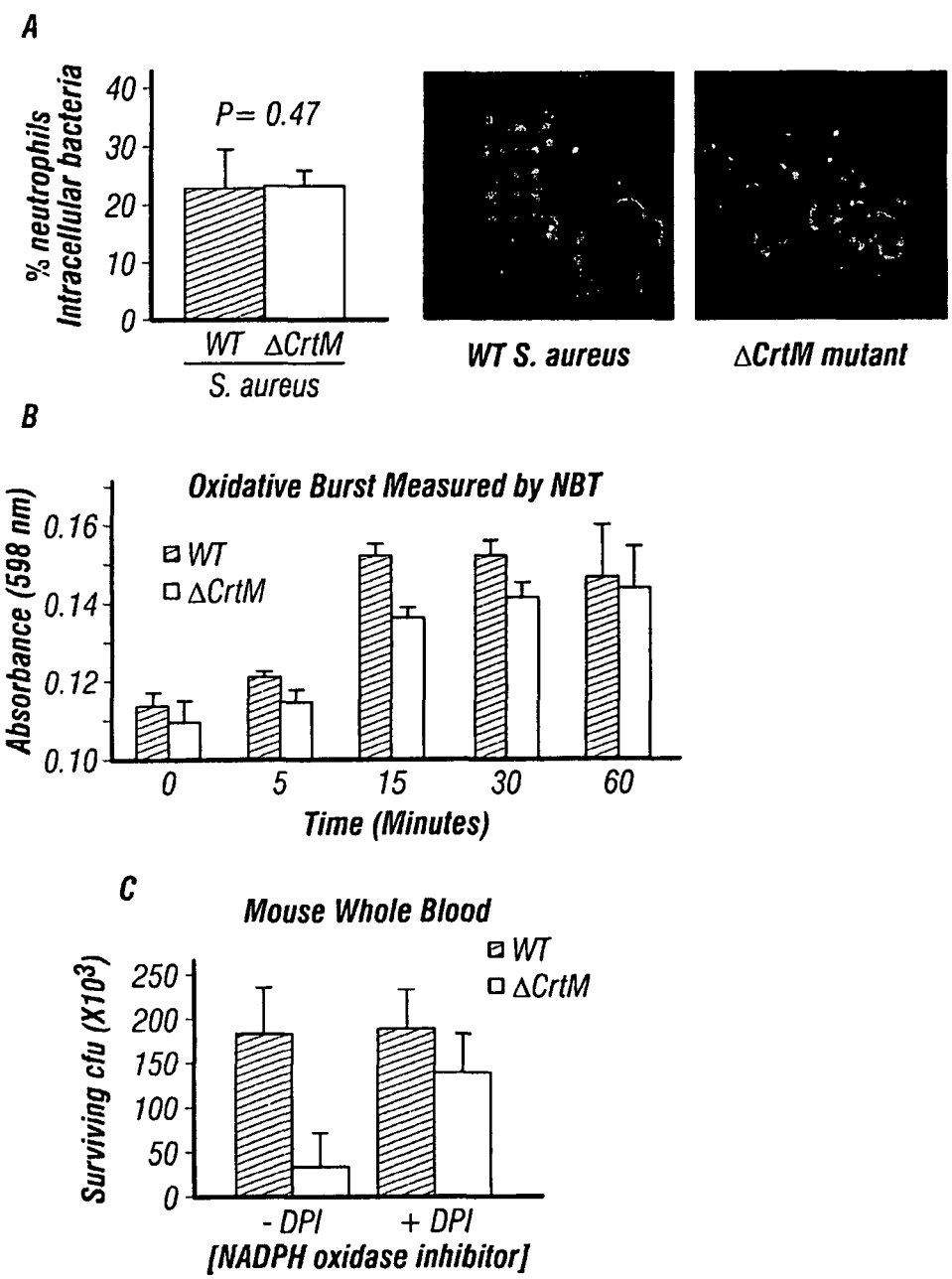
FIG. 6A-F shows a further analyses regarding the antiphagocytic properties of the *Staphylococcus aureus* carotenoid pigment. A) WT and ΔcrtM mutant *S. aureus* are phagocytosed by human neutrophils at a comparable rate. Deconvolution fluorescence microscopy of representative study shows intracellular (green) and extracellular (red) organisms. B) WT and ΔcrtM mutant *S. aureus* provoke similar degrees of human neutrophil oxidative burst as measured by nitroblue tetrazolium reduction. C) Effect of oxidative burst inhibitor diphenyleneiodonium (DPI) on survival of WT and ΔCrtM mutant *S. aureus* in normal mouse blood. Sensitivity of WT and ΔCrtM mutant *S. aureus* strains to killing by D) the granule proteases cathepsin G and human neutrophil elastase or E) the murine cathelicidin mCRAMP. F) Differences in neutrophil intracellular survival between *S. aureus* WT and ΔCrtM mutant *S. aureus* are similar in experiments using preopsonization with autologous serum as those without (e.g.
Figure 6:
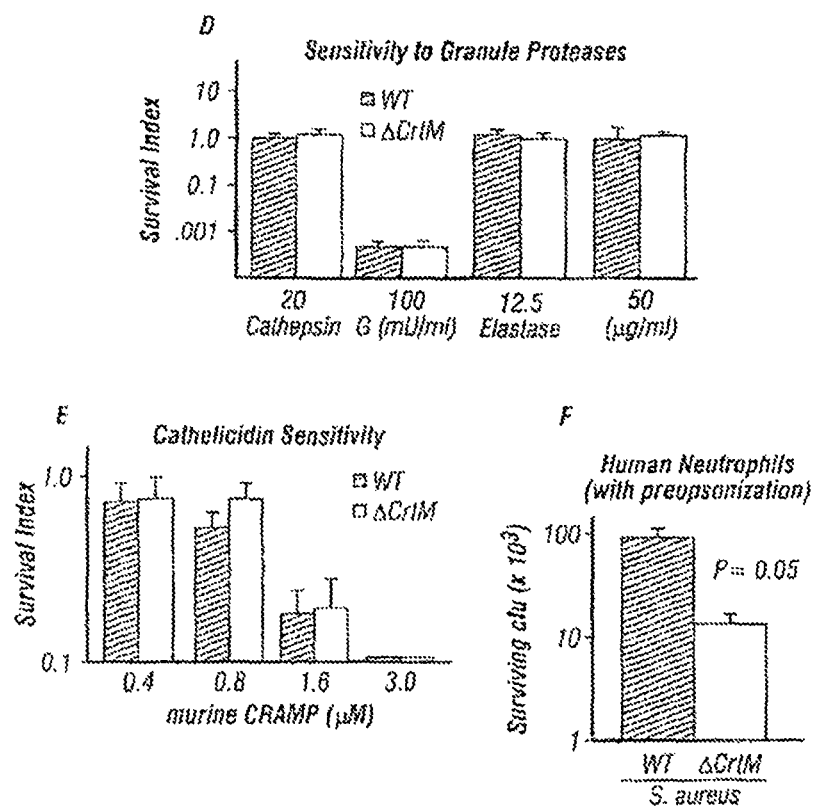

It was then determined whether the observed antioxidant activity of the *S. aureus* carotenoid translated to increased bacterial resistance to innate immune clearance using two ex vivo assay systems: human or mouse whole blood survival and coculture with purified human neutrophils. WT *S. aureus* survived significantly better than the nonpigmented ΔCrtM intracellularly within human neutrophils (FIG. 2a, FIG. 6f) and in whole blood of normal mice or human donors (FIGS. 2b, e). The former effect was not explained by differences in the rate of phagocytosis, since uptake of the WT *S. aureus* and ΔCrtM mutant was comparable (FIG. 6a). Nor were differences attributable to changes in the magnitude of neutrophil oxidative burst, since uptake of WT and mutant strains produced similar results in a nitroblue tetrazolium (NBT) reduction assay (FIG. 6b). Complementation of the *S. aureus* ΔCrtM mutant with pCrtMN restored resistance to killing by mouse whole blood (FIG. 2b). Likewise, the pigmented *S. pyogenes* expressing staphylococcal carotenoid showed enhanced survival in human neutrophils versus the parent strain (FIG. 2c).

To verify the association of S. aureus carotenoid expression with enhanced phagocyte resistance was a direct consequence of its antioxidant properties, assays were repeated in the presence of the oxidative burst inhibitor diphenyleneiodonium (DPI). WT and ΔCrtM S. aureus survived equally well in human neutrophils (FIG. 2d) and mouse blood (FIG. 6c) when oxidative burst was inhibited by DPI. The gp91$^{Phox-/-}$ mouse represents a model of human X-linked chronic granulomatous disease, an inherited defect in phagocyte oxidative burst function. The survival advantage of WT over nonpigmented ΔCrtM S. aureus was evident only in the blood of normal mice (CD1 or C57Bl/6), and not in the blood of gp91$^{Phox-/-}$ mice lacking NADPH oxidase activity (FIGS. 2e, f).

It was recently reported that the apparent neutrophil killing of pathogens by reactive oxygen species could largely reflect the activation of granule proteases mediated through changes in potassium flux. There was no difference in the susceptibility of WT and ΔCrtM S. aureus to the antimicrobial action of cathepsin G, and both strains were resistant to human neutrophil elastase as previously observed for S. aureus[13] (FIG. 6d). Other effector molecules of mammalian neutrophils critical to innate immune defense are the cathelicidin family of antimicrobial peptides[14]. The carotenoid-deficient S. aureus mutant was equally susceptible to killing by the murine cathelicidin mCRAMP when compared to the WT strain (FIG. 6e). These results support a primary role for the free-radical scavenging antioxidant properties of the S. aureus carotenoid in resistance to neutrophil-mediated killing.

Figure 3:
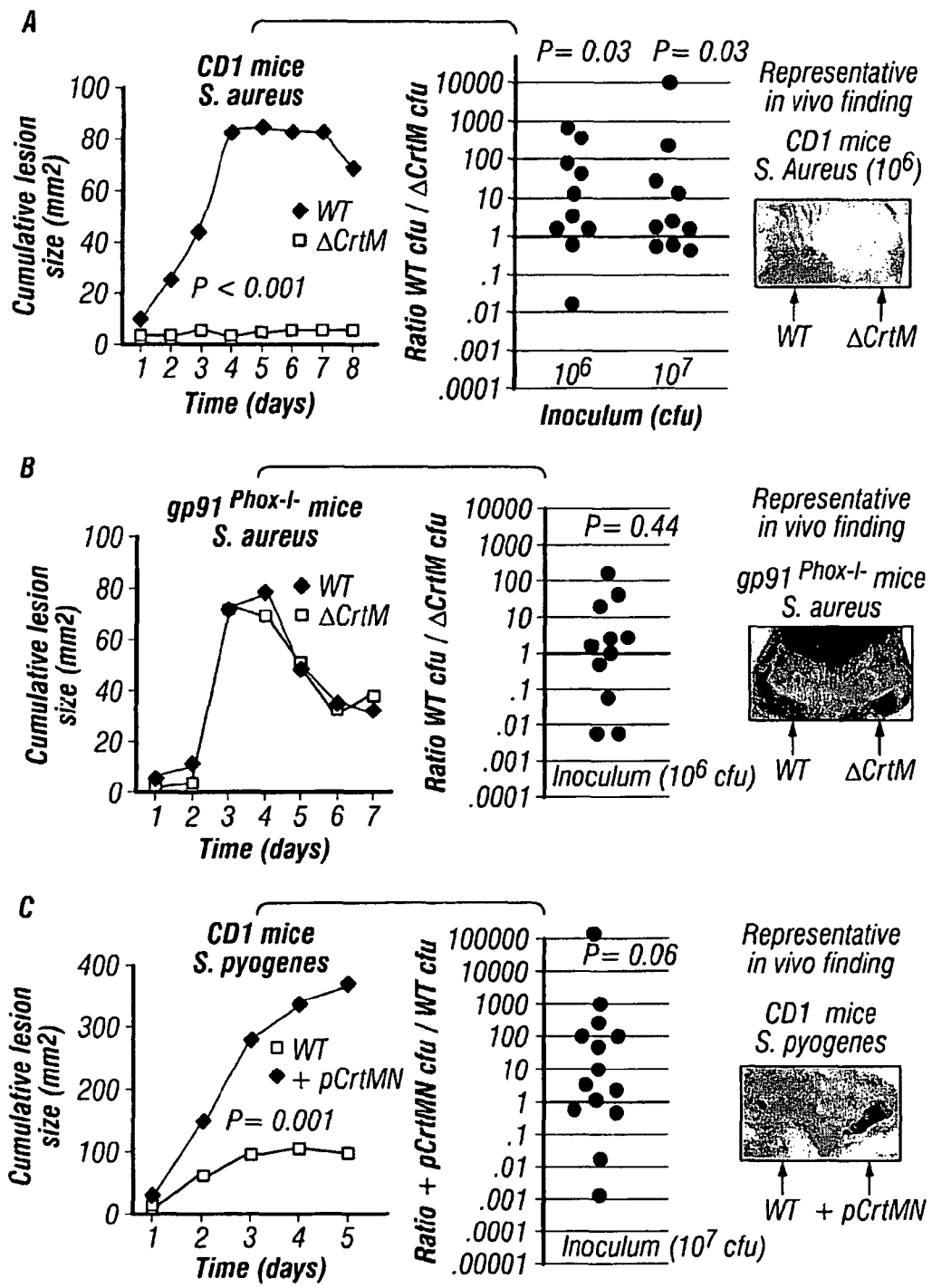
FIG. 3A-C shows *Staphylococcus aureus* carotenoid contributes to virulence in a subcutaneous abscess model. Mice were injected subcutaneously in opposite flanks with the two bacterial strains under comparison. Line graphs depict sum cumulative skin lesion size generated by the indicated bacterial strain. Dots on scatter graphs=ratio of cfu of pigmented vs. nonpigmented strains recovered from skin lesions in each individual mouse. Photographic image depicts representative mouse in each treatment group. A) Wild-type (WT) vs. ΔCrtM mutant *S. aureus* in CD1 mice, B) WT vs. ΔCrtM mutant *S. aureus* in $gp91^{Phox-/-}$ mice, and C) *Streptococcus pyogenes* +/− expression of staphylococcal 4'4'-diaponeurosporene.

The in vitro and ex vivo results demonstrate that S. aureus carotenoid is both necessary and sufficient to promote oxidant resistance and phagocyte survival. To assess the significance of these observations to disease pathogenesis, a murine subcutaneous challenge model was developed. In these studies, individual animals were injected simultaneously in one flank with the WT S. aureus strain and the opposite flank with the ΔCrtM mutant. At the site of WT injection (10$^6$ cfu), mice developed sizeable abscess lesions reaching a cumulative size of 80 mm$^2$ by day 4; injection of an equivalent inoculum of the carotenoid-deficient mutant on the contralateral flank failed to produce visible lesions (FIG. 3a). Quantitative culture from skin lesions at two different challenge doses (10$^6$ cfu to 10$^7$ cfu) consistently demonstrated significantly higher numbers of surviving WT S. aureus compared to the ΔCrtM mutant in the individual mice (FIG. 3a). To corroborate that an antioxidant effect is key to the mechanism of protection afforded by the S. aureus carotenoid in vivo, the subcutaneous infection experiment was repeated in gp91$^{Phox-/-}$ mice. In the absence of host NADPH oxidase function, WT and ΔCrtM mutant S. aureus produced lesions of similar cumulative size and no survival advantage was detected on quantitative abscess culture (FIG. 3b). It was then determined that S. aureus carotenoid was sufficient to enhance bacterial virulence by comparing the course of infection produced by S. pyogenes expressing CrtMN to controls transformed with vector alone. In FIG. 3c, lesions generated by the carotenoid-expressing strain were significantly larger and contained greater numbers of surviving bacteria than those produced by the WT strain. Raw data from the in vivo experiments is provided in Table 1.

TABLE 1

Lesion size and bacterial culture counts from in vivo mouse challenge studies

| Mouse Strain | Bacterial Strain | Dose (cfu) | No. tested | Lesion size (mm$^2$) median/mean | Lesion size (mm$^2$) (Range: low-high) | Lesion culture (cfu) median/mean | Lesion culture (cfu) (Range: low-high) |
|---|---|---|---|---|---|---|---|
| CD1 | S. aureus WT | 10$^6$ | 10 | 5.5/8.2 | 0-42 | 4.8 × 10$^4$/7.0 × 10$^4$ | 1.2 × 10$^3$-3.2 × 10$^5$ |
| CD1 | ΔCrtM mutant | 10$^6$ | 10 | 0.0/0.2 | 0-2 | 1.1 × 10$^4$/1.9 × 10$^4$ | 6.0 × 10$^1$-7.5 × 10$^4$ |
| CD1 | S. aureus WT | 10$^7$ | 10 | 13.0/17.9 | 0-55 | 4.0 × 10$^6$/1.2 × 10$^7$ | 4.4 × 10$^4$-7.9 × 10$^7$ |
| CD1 | ΔCrtM mutant | 10$^7$ | 10 | 2.5/6.8 | 0-32 | 3.8 × 10$^5$/3.3 × 10$^6$ | 7.0 × 10$^2$-1.5 × 10$^7$ |
| Phox$^{-/-}$ | S. aureus WT | 10$^6$ | 11 | 4.0/7.0 | 0-18 | 7.7 × 10$^4$/2.1 × 10$^5$ | 1.6 × 10$^2$-1.2 × 10$^6$ |
| Phox$^{-/-}$ | ΔCrtM mutant | 10$^6$ | 11 | 4.0/6.6 | 0-20 | 4.1 × 10$^4$/1.7 × 10$^5$ | 1.5 × 10$^2$-1.0 × 10$^6$ |
| CD1 | S. pyogenes + vector only | 10$^7$ | 14 | 20.0/22.4 | 0-75 | 6.4 × 10$^7$/1.0 × 10$^9$ | 5.0 × 10$^1$-1.3 × 10$^{10}$ |
| CD1 | S. pyogenes + pCrtMN | 10$^7$ | 14 | 6.0/7.0 | 0-21 | 1.6 × 10$^7$/3.3 × 10$^7$ | 5.0 × 10$^1$-9.0 × 10$^7$ |

Figure 4:
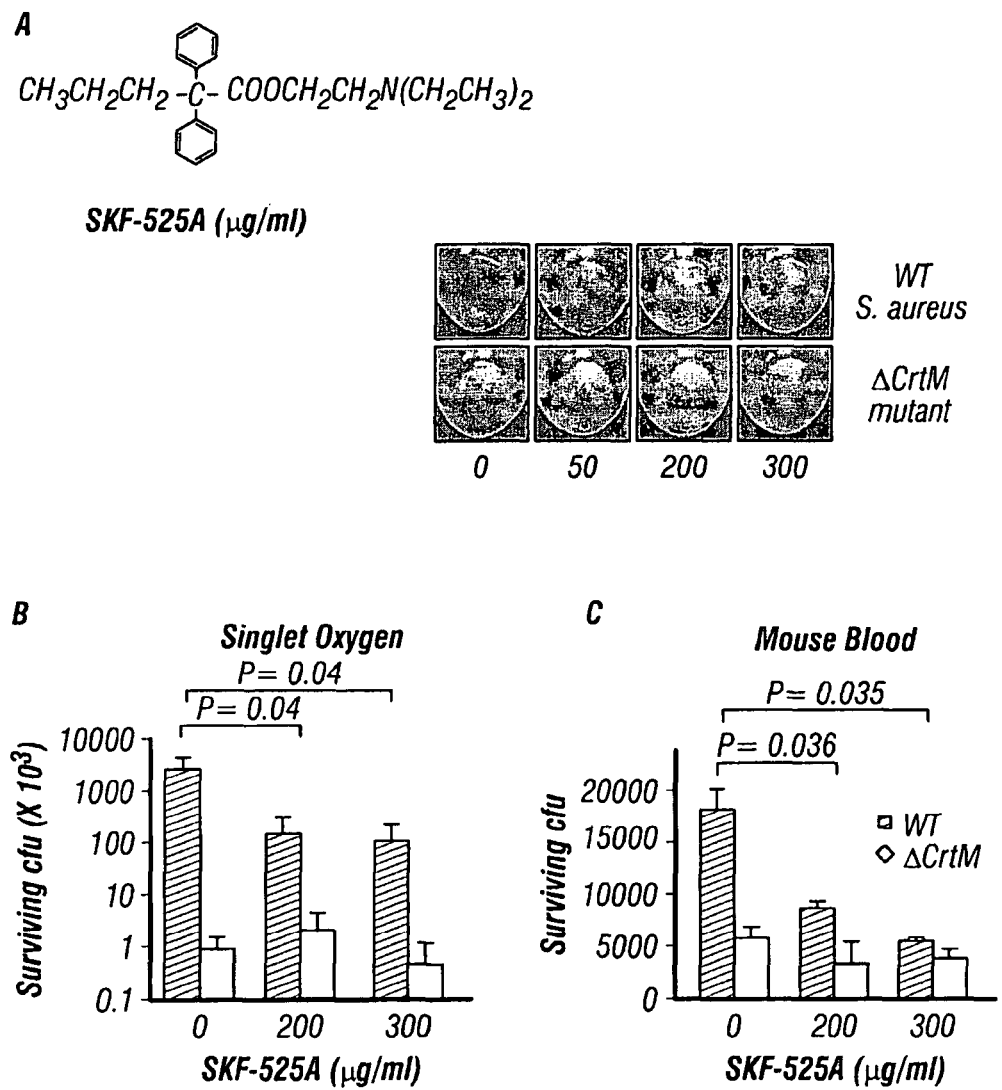
FIG. 4A-B shows the inhibition of *Staphylococcus aureus* pigment production increases oxidant sensitivity and phagocytic clearance. Wild-type and ΔCrtM mutant *S. aureus* were cultured in the presence or absence of SKF 525-A at the indicated concentrations. Depicted are the observed effects on A) pigmentation phenotype, B) singlet oxygen susceptibility, and C) survival in murine whole blood. Results shown are representative of at least three experiments.
Figure 5:
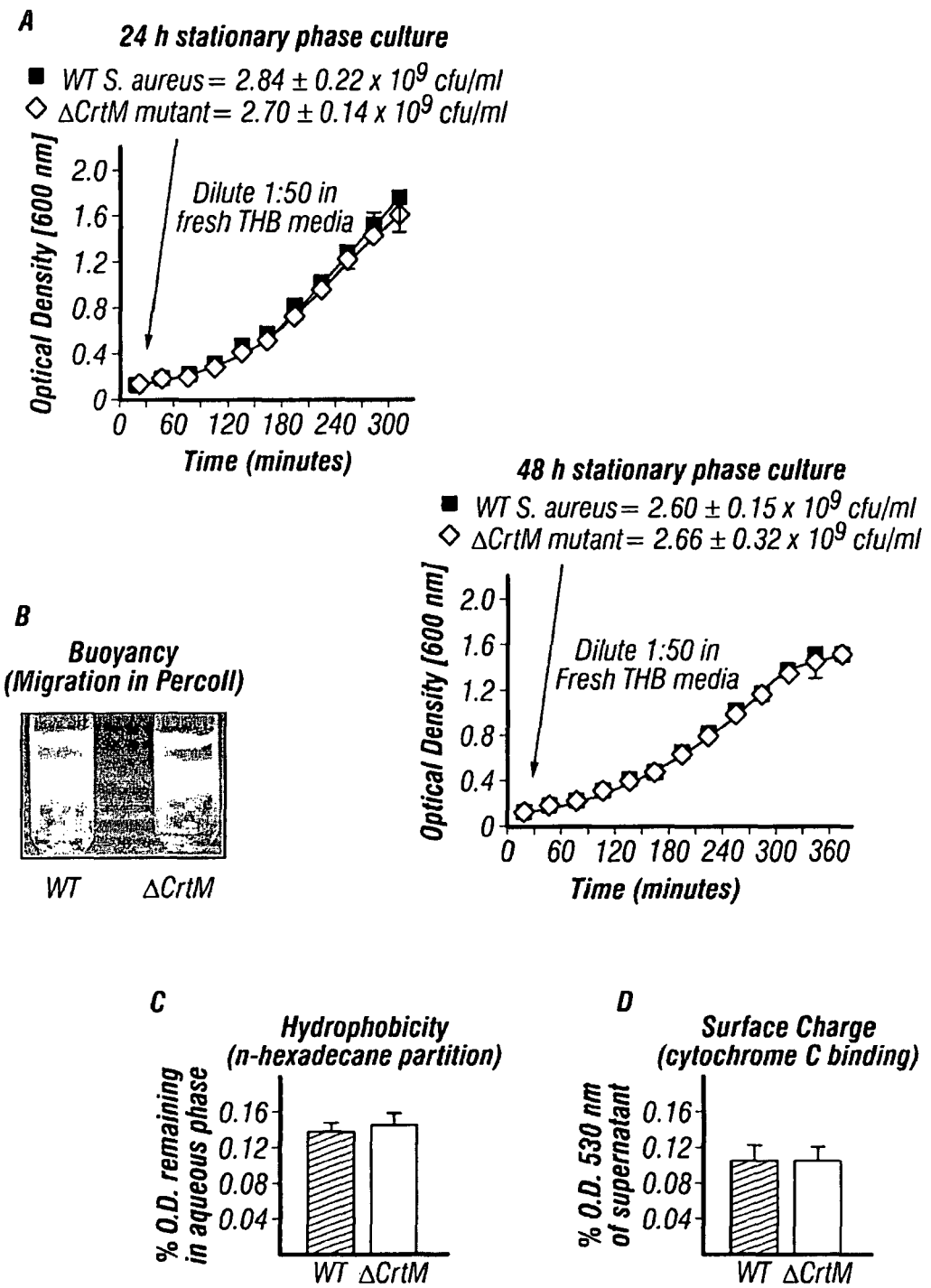
FIG. 5A-D demonstrates a lack of pleiomorphic effects upon allelic replacement of the *S. aureus* crtM gene. A) Similarity of stationary phase concentrations of viable bacteria in stationary phase cultures of WT *S. aureus* vs. ΔcrtM mutant and subsequent growth kinetics of bacteria in fresh THB media. Lack of measurable difference between WT *S. aureus* and ΔcrtM mutant in terms of B) buoyant density assessed by migration in Percoll, C) hydrophobicity as measured by partition into N-hexadecane, and D) surface charge determined by cytochrome C binding.

Given the protective effect provided to the bacteria by the golden yellow pigments, a pharmacologic agent that inhibits carotenogenesis might render S. aureus more susceptible to immune clearance. The mixed function oxidase inhibitor 2-diethylaminoethyl-2,2-diphenyl-valerate (SKF 525-A, Calbiochem) was previously shown to inhibit pigment formation in S. aureus, though a moderate residual accumulation of δ carotenoid intermediate was noted in those experiments. Shown in FIG. 4a, a dose-dependent decrease in pigment production in the WT strain of S. aureus grown in the presence of this agent was obtained. Blocking S. aureus pigment formation led to a dose-dependent increase in the susceptibility of the organism to singlet oxygen killing (FIG. 4b), and a decrease in its ability of WT S. aureus to survive in human whole blood (FIG. 4c). As a control, the ΔCrtM mutant was exposed to SKF 525-A in parallel experiments with no significant effects on oxidant susceptibility or blood survival (FIGS. 4b, c).

Golden color imparted by carotenoid pigments is the eponymous feature of the human pathogen Staphylococcus aureus. A molecular genetic analysis pairing mutagenesis and heterologous expression was performed to show that this hallmark phenotype is in fact a virulence factor, serving to protect the bacterium from phagocytic killing through its antioxidant properties. In the present era, effective control of this important disease agent is compromised by rapid evolution of antimicrobial resistance in both community and hospital settings. In principle, the inhibition of carotenogenesis may offer a novel therapeutic approach to the treatment of complicated S. aureus infections, effectively rendering the pathogen more susceptible to clearance by normal host innate immune defenses.

In addition, WT S. aureus survived significantly better than the nonpigmented ΔCrtM in whole blood of human donors or normal mice and intracellularly within human neutrophils. The latter effect was not explained by differences in the rate of phagocytosis, since uptake of the WT S. aureus and ΔCrtM mutant was comparable. Nor were differences attributable to changes in the magnitude of neutrophil oxidative burst, since uptake of WT and mutant strains produced similar results in a nitroblue tetrazolium (NBT) reduction assay. Complementation of the *S. aureus* ΔCrtM mutant with pCrtMN restored resistance to killing by mouse whole blood or human neutrophils. Likewise, the pigmented *S. pyogenes* expressing staphylococcal carotenoid showed enhanced survival in human neutrophils compared to the parent strain.

To verify the association of *S. aureus* carotenoid expression with enhanced phagocyte resistance was a direct consequence of its antioxidant properties, assays were repeated in the presence of the oxidative burst inhibitor diphenyleneiodonium (DPI). WT and ΔCrtM *S. aureus* survived equally well in human neutrophils and mouse blood when oxidative burst was inhibited by DPI. The gp91$^{Phox-/-}$ mouse represents a model of human X-linked chronic granulomatous disease, an inherited defect in phagocyte oxidative burst function. The survival advantage of WT over nonpigmented ΔCrtM *S. aureus* was evident only in the blood of normal mice (CD1 or C57Bl/6), and not in the blood of gp91$^{Phox-/-}$ mice lacking NADPH oxidase activity.

It was recently reported that the apparent neutrophil killing of pathogens by reactive oxygen species could largely reflect the activation of granule proteases mediated through changes in potassium flux. No difference was identified in the susceptibility of WT and ΔCrtM *S. aureus* to the antimicrobial action of cathepsin G, and both strains were resistant to human neutrophil elastase as previously observed for *S. aureus*. Other effector molecules of mammalian neutrophils critical to innate immune defense are the cathelicidin family of antimicrobial peptides. The carotenoid-deficient *S. aureus* mutant was equally susceptible to killing by the murine cathelicidin mCRAMP when compared to the WT strain. These results support a primary role for the free-radical scavenging antioxidant properties of the *S. aureus* carotenoid in resistance to neutrophil-mediated killing.

The in vitro and ex vivo results demonstrate that *S. aureus* carotenoid is both necessary and sufficient to promote oxidant resistance and phagocyte survival. To assess the significance of these observations to disease pathogenesis, a murine model for subcutaneous challenge was developed. In these studies, individual animals were injected simultaneously in one flank with the WT *S. aureus* strain and the opposite flank with the ΔCrtM mutant. At the site of WT injection mice developed sizeable subcutaneous abscesses, injection of an equivalent inoculum of the carotenoid-deficient mutant on the contralateral flank failed to produce visible abscesses. Quantitative culture from skin lesions consistently demonstrated significantly higher numbers of surviving WT *S. aureus* compared to the ΔCrtM mutant in the individual mice. To corroborate that an antioxidant effect is key to the mechanism of protection afforded by the *S. aureus* carotenoid in vivo, the subcutaneous infection experiment was repeated in gp91$^{Phox-/-}$ mice. In the absence of host NADPH oxidase function, WT and ΔCrtM mutant *S. aureus* produced lesions of similar cumulative size and no survival advantage was detected on quantitative abscess cultures. Furthermore, while *S. pyogenes* infection was associated with development of necrotic ulcers rather than abscess formation, lesions generated by the carotenoid-expressing strain were significantly larger and contained greater numbers of surviving bacteria than those produced by the WT strain.

Given the protective effect provided to the bacteria by the golden yellow pigments, a pharmacologic agent that inhibited carotenogenesis was tested to determine whether the agent might render *S. aureus* more susceptible to immune clearance. The mixed function oxidase inhibitor 2-diethylamino-ethyl-2,2-diphenyl-valerate (SKF 525-A, Calbiochem) was previously shown to inhibit pigment formation in *S. aureus*, and a dose-dependent decrease in carotenoid production was demonstrated in the WT strain of *S. aureus* grown in the presence of the agent. Blocking *S. aureus* pigment formation led to a commensurate dose-dependent increase in the susceptibility of the organism to singlet oxygen killing and a decrease in its ability to survive in human whole blood. As a control, the ΔCrtM mutant was exposed to SKF 525-A in parallel experiments with no significant effects on oxidant susceptibility or blood survival.

Although a number of embodiments and features have been described above, it will be understood by those skilled in the art that modifications and variations of the described embodiments and features may be made without departing from the teachings of the disclosure or the scope of the invention as defined by the appended claims. The appendices attached hereto are provided to further illustrate but not limit the invention.

The invention claimed is:

1. A method of treating a *Staphylococcus* sp, having decreased susceptibility to a vancomycin, or for treating a vancomycin-resistant *Staphylococcus* sp, bacterial infection, comprising:
  (1) providing a pharmaceutical composition comprising a small molecule selected from 2-diethylaminoethyl-2,2-diphenyl-valerate; 2,4-dichloro-6-phenylphenoxyethylamine; 2,4-dichloro-6-phenylphenoxyethyldiethylamine; a piperonyl butoxide; or any combination thereof, that inhibits or slows the production and/or activity of a carotenoid in a bacteria; and
  (2) administering to a subject inflicted with the *Staphylococcus* sp, bacterial infection a therapeutically effective dose of the pharmaceutical composition,
  wherein a therapeutically effective dose inhibits or slows the production and/or activity of a carotenoid in the bacteria, thereby causing the bacteria to be more susceptible to oxidative damage and/or killing by neutrophils, and the therapeutically effective dose is a dose that is not directly cytotoxic to the bacteria.

2. The method of claim 1, wherein the carotenoid is a *Staphylococcus* sp, carotenoid.

3. The method of claim 1, wherein the bacteria is a *Staphylococcus aureus*, or the carotenoid is a *Staphylococcus aureus* carotenoid.

4. The method of claim 1, wherein the small molecule is a mixed function oxidase inhibitor.

5. The method of claim 4, wherein the mixed function oxidase inhibitor comprises a 2-diethylaminoethyl-2,2-diphenyl-valerate; a 2,4-dichloro-6-phenylphenoxyethylamine; a 2,4-dichloro-6-phenylphenoxyethyldiethylamine; a piperonyl butoxide; or any combination thereof.

6. The method of claim 1, wherein the pharmaceutical composition is applied on or with a catheter.

7. The method of claim 1, wherein the small molecule carotenogenesis inhibitor inhibits the activity of or the expression of: a beta-carotene hydroxylase, a p-carotene desaturase; a dehydrosqualene synthase; a dehydrosqualene desaturase; or a combination thereof.

8. A method of treating a *Staphylococcus* sp, bacterial infection, or enhancing the efficacy of a vancomycin treatment for a *Staphylococcus* sp, bacterial infection, to a subject in need thereof, comprising:

(a) providing:
   (i) a pharmaceutical composition comprising a small molecule selected from 2-diethylaminoethyl-2,2-diphenyl-valerate; 2,4-dichloro-6-phenylphenoxyethylamine; 2,4-dichloro-6-phenylphenoxyethyldiethylamine; a piperonyl butoxide; or any combination thereof, that inhibits or slows the production and/or activity of a carotenoid in a bacteria, and
   (ii) a vancomycin;
(2) administering to the subject inflicted with the *Staphylococcus* sp, bacterial infection a therapeutically effective dose of the pharmaceutical composition and the vancomycin,
wherein a therapeutically effective dose inhibits or slows the production and/or activity of a carotenoid in the bacteria, and the therapeutically effective dose is a dose that is not directly cytotoxic to the bacteria, thereby causing the *Staphylococcus* sp, to be more susceptible to oxidative damage and/or killing by neutrophils and enhancing the efficacy of the vancomycin treatment for a *Staphylococcus* sp, bacterial infection.

9. The method of claim 8, wherein the carotenoid is a *Staphylococcus* sp, carotenoid.

10. The method of claim 8, wherein the bacteria is a *Staphylococcus aureus*, or the carotenoid is a *Staphylococcus aureus* carotenoid.

11. The method of claim 8, wherein the small molecule is a mixed function oxidase inhibitor.

12. The method of claim 11, wherein the mixed function oxidase inhibitor comprises a 2-diethylaminoethyl-2,2-diphenyl-valerate; a 2,4-dichloro-6-phenylphenoxyethylamine; a 2,4-dichloro-6-phenylphenoxyethyldiethylamine; a piperonyl butoxide; or any combination thereof.

13. The method of claim 11, wherein the pharmaceutical composition is applied on or with a catheter.

14. The method of claim 11, wherein the small molecule carotenogenesis inhibitor inhibits the activity of or the expression of: a beta-carotene hydroxylase, a p-carotene desaturase; a dehydrosqualene synthase; a dehydrosqualene desaturase; or a combination thereof.

* * * * *